United States Patent
Hayes et al.

[11] Patent Number: 5,899,382
[45] Date of Patent: May 4, 1999

[54] AIR FRESHENER

[75] Inventors: Scott A. Hayes, Wayzata; Alan P. Lonneman, Plymouth, both of Minn.

[73] Assignee: Woodco Manufacturing, Inc., Wayzata, Minn.

[21] Appl. No.: 08/828,399

[22] Filed: Mar. 28, 1997

Related U.S. Application Data

[63] Continuation-in-part of application No. 29/054,965, May 24, 1996, Pat. No. Des. 382,050.
[51] Int. Cl.$^6$ ........................................................ A61L 9/12
[52] U.S. Cl. ................................................. 239/56; 239/57
[58] Field of Search ................................. 239/34, 44, 53, 239/55, 56, 57

[56] References Cited

U.S. PATENT DOCUMENTS

| | | |
|---|---|---|
| D. 372,526 | 8/1996 | Rymer . |
| D. 373,626 | 9/1996 | Dente et al. . |
| 2,988,284 | 6/1961 | Smith . |
| 3,685,734 | 8/1972 | Paciorek et al. . |
| 4,158,440 | 6/1979 | Sullivan et al. . |
| 4,523,870 | 6/1985 | Spector . |
| 4,813,344 | 3/1989 | Greif . |
| 4,960,240 | 10/1990 | McElfresh . |
| 5,076,436 | 12/1991 | Bortolani et al. ................... 206/497 X |
| 5,098,713 | 3/1992 | Mattesky . |
| 5,259,555 | 11/1993 | Kiefer ....................................... 239/35 |
| 5,269,723 | 12/1993 | Bender . |
| 5,282,571 | 2/1994 | Smith et al. .......................... 239/34 X |
| 5,429,301 | 7/1995 | Franks . |
| 5,551,557 | 9/1996 | Brooks et al. ....................... 206/497 X |
| 5,575,992 | 11/1996 | Kanee .................................. 239/34 X |

*Primary Examiner*—Kevin Weldon
*Attorney, Agent, or Firm*—Burd, Bartz & Gutenkauf

[57] ABSTRACT

A device for releasing a volatile substance into an environment in a controlled/metered manner. A reservoir made of a substance-absorbent material that is impregnated with a volatile substance in its liquid phase is located in a cavity open at the front surface of a container body made of a material non-permeable to the substance. A wood or wood-type panel permeable to the substance covers the cavity. A clip may be fixed to the back surface of the container body so that the device may be secured to a mounting surface. The device may be packaged with skin pack film such that a vapor barrier is formed, preserving/storing the substance until such time as opened/activated by the consumer. When activated, a volatilization mechanism is initiated wherein the panel absorbs the substance from the reservoir, the substance is introduced to ambient air, volatilized, released and, finally, dispersed throughout an environment.

12 Claims, 2 Drawing Sheets

AIR FRESHENER

CROSS-REFERENCE TO RELATED APPLICATION

This application is a continuation-in-part of U.S. patent application Ser. No. 29/054,965 filed on May 24, 1996 now U.S. Pat. No. Des. 382,050.

BACKGROUND OF THE INVENTION

1. Field of the Invention

This invention relates generally to a device for releasing a volatile substance into an environment in a controlled/metered manner. In particular, this invention relates to an air freshener that, once opened/activated, uniformly and continuously releases a volatile fragrance/deodorant into the atmosphere surrounding it.

2. Description of the Prior Art

Products that dispense fragrances, deodorants and the like are well known and available in many forms. Many of these products utilize substances that are volatile. Volatile substances can be released into an environment through mere exposure to ambient air. When exposed to the atmosphere, a volatile substance converts from its solid, liquid, gel or other non-vapor form to a vaporous one. Once released, the vaporous emissions are dispersed, that is, they travel through the air to treat the surrounding environment.

Air fresheners that utilize volatile fragrances/deodorants typically include some type of container, holder or other housing. A variety of container types can be found on supermarket shelves and, while the containers differ radically in shape, size and materials used, all include some means by which the container may be sealed to effectively store/preserve the volatile fragrance/deodorant until such time as opened/activated by the consumer.

Also common to many air fresheners is the capacity to, once opened/activated, release a fragrance/deodorant into an environment in a controlled/metered manner, that is, maintain a continuous, uniform release rate for an extended period of time while the amount of substance initially present in the device is volatilized.

Exemplary of the various mean and methods for containing and sealing volatile substances and for controlling/metering the rate of release of vapors from them are as follows.

U.S. Pat. No. 4,960,240 (McElfresh) discloses an air freshener comprising a unitary container made of molded plastic comprising two partial enclosures adapted to be folded about a hinge and sealed together to form a generally flat, hermetically sealed enclosure. The sealed container is adapted to retain an active, vaporizable substance bearing member. One portion of the sealed container is provided with an integrally formed tear-away tab adapted to be removed by a user prior to use of the air freshener.

U.S. Pat. No. 4,523,870 (Spector) discloses an aroma dispensing cartridge and holder assembly attachable to an air vent in the interior of an automobile. The assembly is constituted by a holder provided with an array of parallel slots and a replaceable cartridge which is telescoped therein. The cartridge contains a porous pad impregnated with liquid scent and includes a further array of slots. The inserted cartridge is axially shiftable relative to the holder from an inactive position in which the holder and cartridge slots are out off registration to effectively seal the pad, to an active position in which the slots lie in registration, as a consequence of which the forced stream from the vent passes through the porous pad to volatilize the liquid scent and diffuse it within the automobile.

U.S. Pat. No. 2,988,284 (Smith) discloses a device comprised of a block made of wood, pulp, gum or the like which is impregnated with a fragrance and then hermetically sealed in an air-tight vapor-impermeable coating. One or more holes are drilled into the block through the coating and fragrance is emitted therefrom. Vaporization of the fragrance is controlled by the relatively small exposed surface area of the hole compared to the volume of the entire block.

Other means and methods for controlling/metering the release and dispersal of volatile substances found in the prior art are more exacting.

U.S. Pat. No. 4,158,440 (Sullivan) discloses a device comprising a reservoir of substance-absorbent material, for storing the substance, that is encapsulated in an envelope. At least a portion of the envelope comprises a permeable material which has porosity at least equal to ultramicroporosity. The permeable envelope portion has a greater affinity for the substance than does the reservoir material. The remainder of the envelope comprises a material impermeable to the substance. To activate the device, a hole is made in the envelope, exposing at least a portion of the ultramicroporous sheet to the environment. The substance permeates through the permeable envelope portion to be released therefrom in vapor form into the environment at a uniform rate.

U.S. Pat. No. 3,685,734 (Paciorek et al.) discloses a controlled fragrance release device which includes a substrate layer on which a layer of vinyl plastisol resin containing an essential oil or other volatile substance is coated. A cover ply is placed over the resin layer to contain the volatile substance until removed.

As is demonstrated in the prior art to varying degrees, a device whose object is to maintain a continuous, uniform volatile substance release rate for an extended period of time while the amount of substance initially present is volatilized is not novel.

The present invention is unique, however, in that the metering instrument utilized to control the rate of volatilization of the substance is a wood panel. Unlike the Smith patent, where a wood block suffused with fragrance is sealed with an impermeable coating, the present invention teaches a fragrance/deodorant-retaining reservoir in abutting contact with, but discreet from, the wood member.

Wood is a desirable absorptive medium not only because it is inherently porous, its appearance also provides consumers with a unique, stylishly organic and attractive alternative to the many predominantly plastic models of air freshening devices on the market today. Such is one object of the invention.

Another object of the invention is to provide an air freshener that is easily activated upon demand, that is, whose sealing means may be removed by the consumer with little effort. Tear-away tabs, removable cover plies and other means demonstrated in the prior art accomplish this object but, while effective, their use necessitates use of materials and processes in addition to those associated with whatever exterior packaging a device is shipped and/or sold in. These additional materials and processes can be expensive. It is a further object of the present invention to provide an air freshener that is economical in its efficiency. Skin pack film is vacuum sealed over the volatilizing/active surface of the device, the aforementioned wood panel, to a flat porous card. The film creates a barrier that prevents exposure of the panel to air, thereby preserving the volatile substance until such time as it is needed. The consumer may activate the device by simply peeling the film away from it and the card.

Most air fresheners are designed with consumer convenience in mind, but a wood block can be bulky and heavy and, therefore, cumbersome and does not lend itself practically to affecting the atmosphere in small areas, and plastic films and vinyls can be delicate and may require additional protective housing or limited in their application. It is yet another object of the present invention to provide an air freshener that is small and light yet durable and remarkably adaptable.

Many products for dispensing fragrances and deodorants available today are designed to be simply set upon a stationary flat surface, such as a counter top or table, in the area targeted for treatment. Less accommodating areas/surfaces require more sophisticated means of insuring the device stays in place.

The McElfresh patent discloses an adhesive means, such as double-stick tape, to mount the air freshener to a surface in the area to be treated.

The Spector patent teaches use of a cruciform releasable clip to be attached to an automobile air vent at the front and middle of same.

U.S. Pat. No. 4,814,344 (Grief) discloses an automobile air freshener with means for attaching same that include cooperating Velcro-type attaching elements, one carried by the air freshener container bottom, the other carried by the louvre blade of an automobile air vent.

It is a yet a further object of the present invention to provide an air freshening device that is versatile, in that it can be temporarily, yet securely, attached to a variety of mounting surfaces. A clip fixed to the device container allows its user to quickly and easily attach it to or remove it from most surfaces, including the sun visor of an automobile, requiring no time consuming peeling-off of tapes and the like and leaving no messy adhesive residues.

SUMMARY OF THE INVENTION

Broadly stated, these and other objects, aspects and advantages of the invention are achieved by or will be understood from the preferred embodiment in the form of a device comprising: a reservoir made of substance-absorbent material that is non-reactive and impregnated with a volatile substance in its liquid phase. The reservoir is located in a cavity open at the front surface of a container made of a material impermeable to the substance. A wood or wood-type panel permeable to the substance covers the cavity opening. A clip may be fixed to the container so that it may be secured to a mounting surface. The device may be packaged with skin pack film such that a vapor barrier is formed, preserving/storing the substance until such time as opened/activated by the consumer. When activated, a volatilization mechanism is initiated wherein the panel absorbs the volatile substance from the reservoir, the substance is introduced to ambient air from the exterior surface of the panel, volatilized, released and, finally, dispersed throughout an environment.

DETAILED DESCRIPTION OF THE PREFERRED EMBODIMENT

Figure 1:
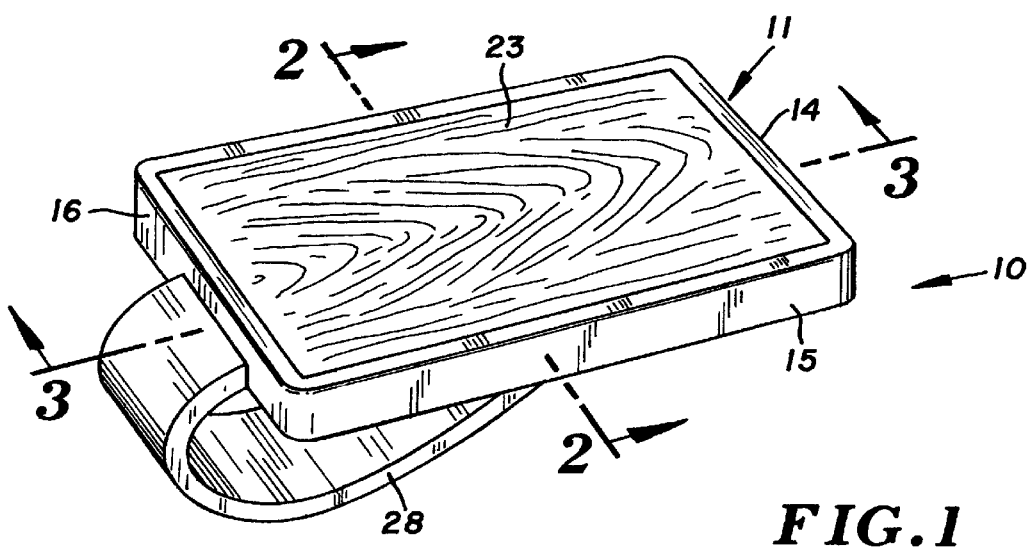
FIG. 1 is a perspective view of an air freshener according to a preferred embodiment of the invention.
Figure 2:
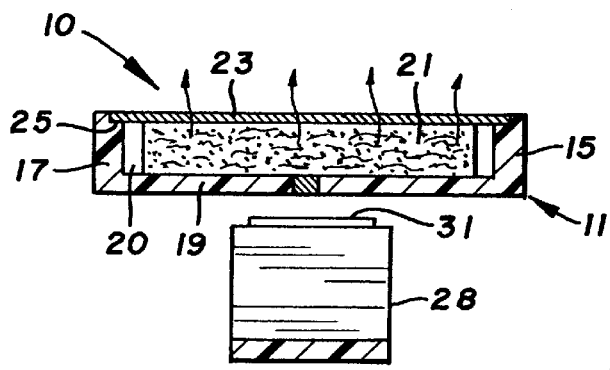
FIG. 2 is an enlarged sectional view of the air freshener of FIG. 1 taken along the line 2—2 thereof.
Figure 3:
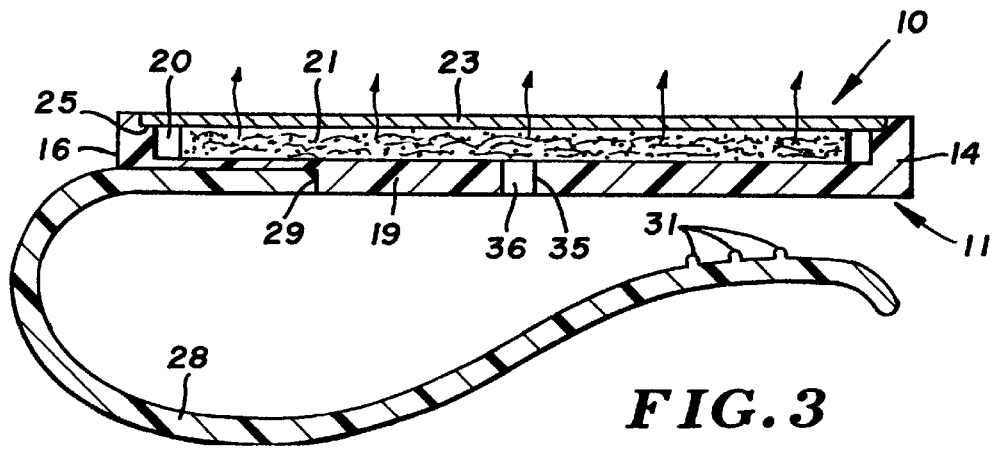
FIG. 3 is an enlarged sectional view of the air freshener of FIG. 1 taken along the line 3—3 thereof.

Referring to the drawings, there is shown in FIGS. 1 through 3 a device for releasing a volatile substance into an environment in a controlled/metered manner. The substance may be a fragrance or volatile liquid or oil carrying a fragrance, a fragrant liquid deodorizer, insecticide, germicide or other material. Exemplary of environments that may be treated are automobile and other motor vehicle interiors, trailers, cupboards and drawers, garbage containers and rooms.

In the preferred embodiment shown in the drawings, the present invention relates to a device for an air freshener indicated generally at 10. Air freshener 10 includes a housing or container body 11 having side walls 14, 15, 16 and 17 connected in perpendicular orientation to a back wall 19. The side and back walls define an interior chamber or cavity 20 open at the front of the body 11. A substance-absorbent reservoir 21 is located in the cavity 20. A permeable panel 23 closes the front opening to the body 11, enclosing the reservoir 21 in the cavity 20. The front facing edges of the side walls have a peripheral, inwardly-facing ledge 25. Ledge 25 forms a seat for the panel 23 which is secured thereon by any suitable and preferred means.

Reservoir 21 is made of a substance-absorbent material, such as blotting paper-type material, pressed cotton, cellulose, expanded foam or other such porous and absorbent natural or synthetic material, that is non-reactive with the volatile substance to be used. When located in the cavity 20 and preparatory to use, the reservoir 21 is charged or impregnated with a supply of the substance. Reservoir 21 is preferably in surface contact with the inward-facing surface of panel 23.

Panel 23 is a relatively thin member made of a wood-type material selected for its permeability characteristics, primary of which are that it be permeable to the particular volatile substance retained in the reservoir 21, and function to effect the release of same substance in a controlled/metered manner. The rate of release and dispersement of the substance is affected by the permeability coefficient of the panel 23 material as well as the thickness and surface area of the panel. The panel 23 is preferably made of wood because wood is, altogether, aesthetically pleasing, highly available, inexpensive, recyclable and inherently porous and self-metering.

Container body 11 is made of any suitable, relatively rigid material that is impermeable to and non-reactive with the volatile substance being used. Such materials include wood, resin and metal. Means are fixed to the body 11 so that it may be secured to a mounting surface, such as the sun visor of an automobile. As shown in FIG. 3, a clip 28 is fixed to the exterior of the back wall 19. Clip 28 is generally fish-hook in shape and relatively resilient. The fixed end of the clip sits in a notch 29 formed on the back wall 19 and is retained therein by suitable means, such as weld or glue. The clip 28 has a plurality of ribs 31 in confronting relationship to the surface of back wall 19. The ribs 31 cooperate with clip 28 in securing the body 11 to a mounting surface.

Figure 4:
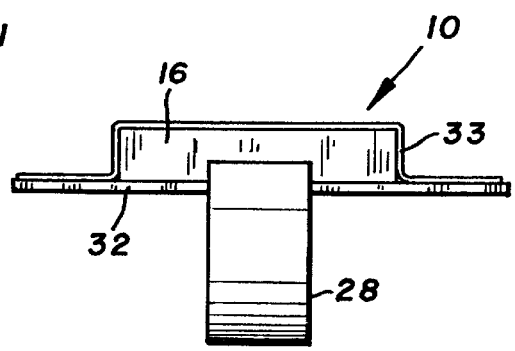
FIG. 4 is an end view of the air freshener of FIG. 1 showing a packaging scheme for the device.

A packaging scheme for the air freshener 10 is depicted in FIG. 4. To avoid premature depletion of the supply of volatile substance, it is necessary that the exposed surface of panel 23 be covered prior to activation and use of the device 10. This preservation is accomplished by the packaging scheme. The device 10 is mounted on a display card 32 such that the back wall 19 of the container body 11 abuts the card. The clip 28 passes through a cut-out opening 34 in the display card (see FIG. 5). Skin pack film 33 covers the device 10, and in particular panel 23, preventing premature release and dispersal of the volatile substance. The card 32 may present an attractive display advertising the product, carry instructions on the product's use and like information. The device 10 is automatically activated when the consumer removes it from the film 33.

Figure 5:
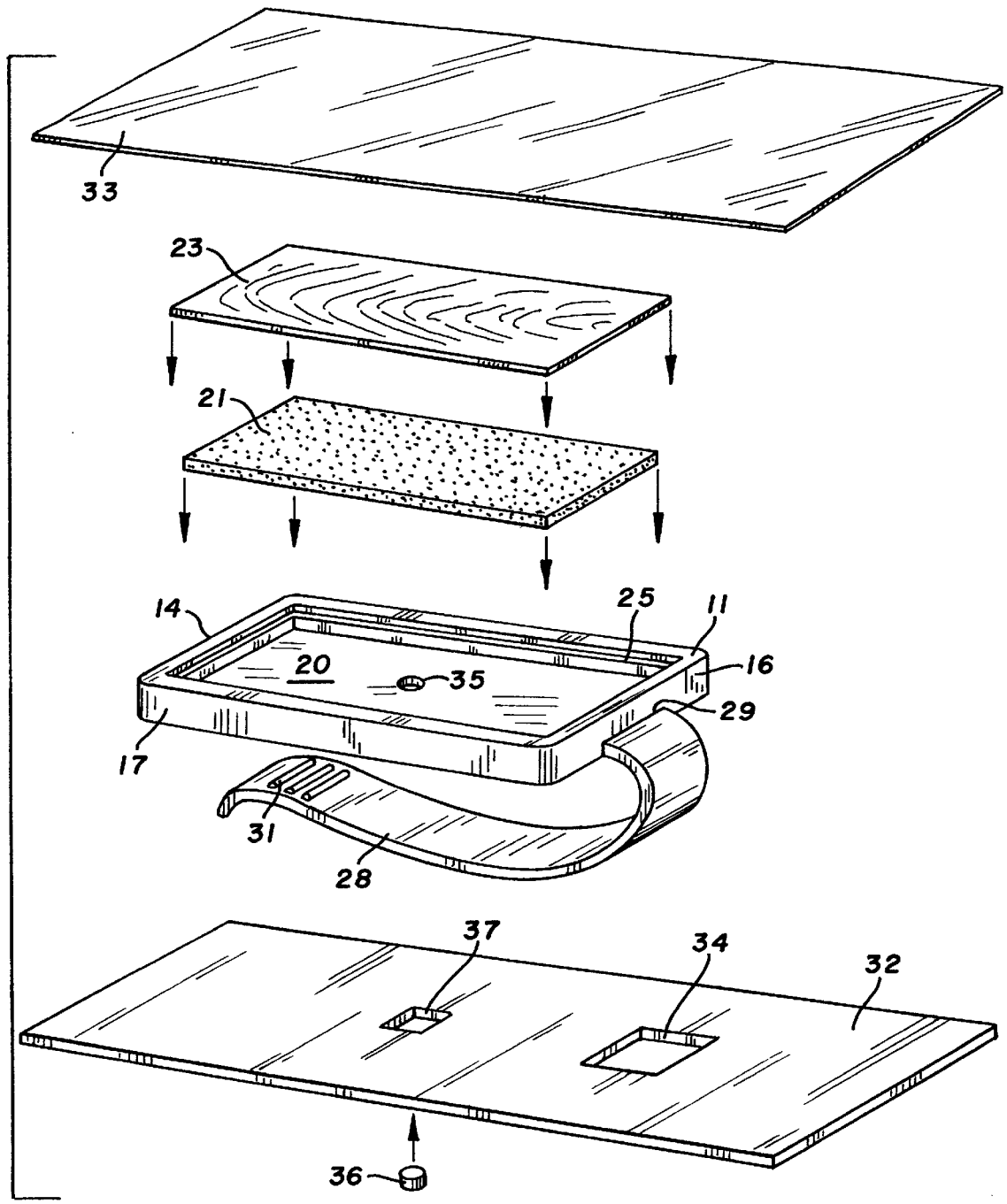
FIG. 5 is an enlarged assembly view of the air freshener of FIG. 1.

An assembly scheme for the air freshener 10 is depicted in FIG. 5. Container body 11 includes a hole 35 open from outside of cavity 20 to the cavity interior. Hole 35 passes through back wall 19. In assembly, reservoir 21, empty of substance, is placed in cavity 20 as indicated in FIG. 5. Panel 23 is fixed over the front opening to body 11, closing the front opening and enclosing reservoir 21. The container body 11 is mounted on the display card 32 in the aforementioned manner and the skin pack film 33 is applied. In addition to the cut-out opening 34 through which the clip 28 passes, the display card 32 includes a suitable access opening 37, making the hole 35 in the body 11 accessible from the exterior after packaging. A suitable instrument is used to access the cavity 20 through hole 35 and draw air from it, thereby creating a vacuum. The same instrument, or another suitable one, such as a needleless syringe having an injection hub, is used to inject a supply of volatile substance into the cavity through the hole 35. The relative vacuum in the cavity 21 facilitates its filling with substance. When the cavity has been filled, the hole 35 is closed as with the plug 36 shown in FIGS. 3 and 5. The plug 36 may be held in place by press fit, hot melt glue or the like.

In the alternative, the reservoir 21 may be impregnated with the product prior to being assembled in the container body 11, omitting the hole 35 and the plug 36.

To activate the device 10, the consumer need merely peel the skin pack film 33 away from it and the card 32. By exposing the wood-type panel 23 to the atmosphere, the user initiates the volatilization mechanism, that is, the panel absorbs the volatile substance from the reservoir 21, the substance is introduced to ambient air from the exterior surface of the panel 23, is volatilized and released and, finally, dispersed throughout an environment.

While there has been shown and described a preferred embodiment of the air freshener of the invention, it is understood that changes in structure, arrangement of structure, and materials may be made by those skilled in the art without departing from the invention. The invention is defined in the following claims.

We claim:

1. A device for releasing a volatile substance into an environment in a controlled manner, said device comprising:

A. a container body having a back wall and sidewalls connected to the back wall, said sidewalls having front edges defining a cavity open at the front of the body, said body composed of a material impermeable to the substance;

B. a reservoir formed of a porous substance-absorbent material non-reactive with the substance and located in and substantially filling said cavity; and C. a panel permeable to the substance, disposed between the front edges of the sidewalls of the body so as to cover said cavity opening, said panel formed of wood and being relatively thin and of uniform thickness, said reservoir in surface contact with said panel;

whereby the reservoir may be filled with the volatile substance and, when the device is filled, the substance is absorbed by and permeates through the panel and is released in vapor form into the atmosphere surrounding the device.

2. The device of claim 1 wherein said container body is composed of polyethylene resin.

3. The device of claim 1 wherein said container body is composed of polypropylene resin.

4. The device of claim 1 wherein said reservoir of substance-absorbent material is composed of a natural open cell material.

5. The device of claim 1 wherein said reservoir of substance-absorbent material is composed of a synthetic open cell material.

6. The device of claim 1 wherein said volatile substance is a fragrant oil.

7. The device of claim 1 wherein said volatile substance is a fragrant liquid deodorizer.

8. The device of claim 1 wherein said container body and cavity and wood-type panel are rectangular in shape.

9. The device of claim 1 further comprising: a ledge surrounding the interior perimeter of the cavity recessed from the plane of the front surface of the body.

10. The device of claim 9 wherein the area of the wood-type panel is slightly less than the area of the exterior perimeter of said ledge.

11. The device of claim 1 further comprising: means for securing said device to a mounting surface wherein:

A. said securing means is a fishhook-shaped clip;

B. said clip is composed of polyethylene or polypropylene resin; and

C. said clip is attached to the body.

12. The device of claim 1 further comprising: means vacuum sealing the device wherein:

A. said sealing means is skin pack film;

B. said skin pack film covers the front surface of the container body, preventing the volatile substance from dissipating, and wherein removal of the film from the device triggers volatilization of said substance.

* * * * *